(12) United States Patent
Sarvazyan

(10) Patent No.: US 7,033,321 B1
(45) Date of Patent: Apr. 25, 2006

(54) ULTRASONIC WATER CONTENT MONITOR AND METHODS FOR MONITORING TISSUE HYDRATION

(75) Inventor: Armen P. Sarvazyan, Lambertville, NJ (US)

(73) Assignee: Artann Laboratories, Inc., Lambertville, NJ (US)

(*) Notice: Subject to any disclaimer, the term of this patent is extended or adjusted under 35 U.S.C. 154(b) by 0 days.

(21) Appl. No.: 10/979,940

(22) Filed: Oct. 25, 2004

(51) Int. Cl.
*A61B 8/02* (2006.01)

(52) U.S. Cl. ..................................... 600/449

(58) Field of Classification Search ................ 600/438, 600/449, 456; 73/597
See application file for complete search history.

(56) References Cited

U.S. PATENT DOCUMENTS

| 4,008,712 | A | | 2/1977 | Nyboer |
| 4,383,533 | A | * | 5/1983 | Lovelace et al. ........... 600/437 |
| 4,635,198 | A | * | 1/1987 | Hohlweck et al. .......... 600/448 |
| 5,152,293 | A | | 10/1992 | Vonesh |
| 5,453,576 | A | * | 9/1995 | Krivitski ..................... 600/481 |
| 5,615,689 | A | | 4/1997 | Kotler |
| 5,720,290 | A | * | 2/1998 | Buhler et al. ............... 600/449 |
| 5,935,066 | A | | 8/1999 | Harris |
| 6,125,297 | A | | 9/2000 | Soconolfi |
| 6,135,964 | A | * | 10/2000 | Barry et al. ................. 600/449 |
| 6,221,019 | B1 | | 4/2001 | Kantorovich |
| 6,280,396 | B1 | | 8/2001 | Clark |
| 6,328,694 | B1 | | 12/2001 | Michaeli |
| 6,458,084 | B1 | * | 10/2002 | Tsao et al. ................... 600/443 |
| 6,459,930 | B1 | | 10/2002 | Takehara |
| 6,517,487 | B1 | * | 2/2003 | Mazess et al. .............. 600/449 |
| 6,579,244 | B1 | * | 6/2003 | Goodwin ..................... 600/561 |
| 6,702,743 | B1 | | 3/2004 | Michaeli |

FOREIGN PATENT DOCUMENTS

JP 2003339699 * 12/2003

* cited by examiner

*Primary Examiner*—Francis J. Jaworski
(74) *Attorney, Agent, or Firm*—Boris Leschinsky (57) ABSTRACT

A device and method for determining the hydration and water content status of soft biological tissue is disclosed and includes a couple of ultrasonic transducers located at a known distance therebetween and held against the tissue of interest as well as an adjustable support system with angle measuring means necessary for evaluation of ultrasound velocity in this tissue. Based on the time-of-flight results of the ultrasound velocity measurement, the water content in the tested tissue is evaluated and the hydration status is determined. One embodiment of the invention is a wearable device attached to human calf measuring water content in muscle.

15 Claims, 11 Drawing Sheets

ULTRASONIC WATER CONTENT MONITOR AND METHODS FOR MONITORING TISSUE HYDRATION

BACKGROUND OF THE INVENTION

The present invention relates generally to ultrasonic measurements of biological tissue parameters for medical diagnostics, and more particularly to a method and a device for measurements of ultrasound velocity in tissue aimed at determination of hydration and water content status of selected tissue or the entire human body.

Tissue water content, a specifically, muscle water content (MWC), is an important and informative diagnostic parameter. Dehydration decreases cognitive and physical work capabilities, while the excessive hydration (swelling, edema) is a common symptom of cardiac, hepatic or renal pathology, malnutrition and many other pathologies and diseases. Edema causes muscle aches and pains and may affect the brain, causing headaches and irritability. Edema is a major symptom for deep venous thrombosis. It may be caused by allergies or more serious disorders of the kidney, bladder, heart, and liver, as well as food intolerance, poor diet (high sugar & salt intake), pregnancy, abuse of laxatives, diuretics, drugs, the use of contraceptive pills, hormone replacement therapy, phlebitis, etc.

Monitoring of muscle water content can serve as an important indicator of body hydration status in athletes during the training as well as in soldiers during deployment. It is generally known that body hypohydration causes severe complications, health and performance problems. It is generally known that a body water weight loss of up to 1% causes thirst, 2%—vague discomfort and oppression, 4%—increased effort for physical work, 5%—difficulty concentrating, 6%—impairment in exercise temperature regulation, increases in pulse and respiratory rate; 10%—spastic muscles; 15%—death. Soldiers commonly dehydrate 2–5% of body weight due to high rate of water loss from environmental exposure and performing stressful physical work. Dehydration by modest amounts (2%) decreases cognitive and physical work capabilities, while larger water losses have devastating effects on performance and health. Numerous pathologic signs and symptoms due to body dehydration include digestion problems, high blood pressure, muscle cramps, etc. MWC monitoring by an objective instrument may help prevent hazard thresholds. This is important because subjective indicators like thirst can be inadequate.

Control of MWC in athletes and soldiers could help in monitoring total body hydration during long-term endurance exercise or performance in hot weather conditions.

There are several methods for assessing total body water, as the most prominent indicator of hydration status. Most of these methods are based on bioelectrical impedance and conductance methods. U.S. Pat. No. 4,008,712 issued to Nyboer discloses method and apparatus for performing electrical measurement of body electrical impedances to determine changes in total body water in normal and deranged states of the body, U.S. Pat. No. 5,615,689 issued to Kotler discloses a method of predicting body cell mass using impedance analysis, U.S. Pat. No. 6,280,396 issued to Clark discloses an apparatus and method for measuring subject's total body water content by measuring the impedance of the body, and U.S. Pat. No. 6,459,930 issued to Takehara et al. discloses a dehydration condition judging apparatus by measuring bioelectric impedance.

The aqueous tissues of the body, due to their dissolved electrolytes, are the major conductors of an electrical current, whereas body fat and bone have relatively poor conductance properties. Significant technical problems eliminated the viability of many electrical methods for in vivo body composition analyses. Oversimplifications in formulae in the standard biological impedance analysis methods lead to problems. There is a more complex approach, based on measuring resistance and reactance over a wide range of frequencies. The technique based on this approach is called bioelectrical impedance spectroscopy. U.S. Pat. No. 6,125,297 issued to Siconolfi discloses a method and apparatus for determining volumes of body fluids in a subject using bioelectrical response spectroscopy.

Regardless of the choice of single or multifrequency method, the impedance index alone is not an accurate predictor. Additional anthropometric terms (i.e., weight, age, gender, race, shoulder width, girth, waist-to-hip ratio, body mass index) need to be included in the prediction model to reduce the standard error of the estimate. In summary, the downside of the water content assessment methods based on the measurements of electrical properties of tissues is low accuracy, significant dependence of testing results on the anthropometrical features of the subject and on electrolyte balance.

There are existing much more precise laboratory methods of assessment of body water content such as Magnetic Resonance Imaging and various so called Dilution methods, but these methods use bulky equipment, are lengthy and laborious to perform and are impractical for most applications. The basic principle of the dilution techniques for body water content is that the volume of a compartment can be defined as the ratio of the dose of a tracer, administered orally or intravenously, to its concentration in that body compartment within a short time after the dose is administered. Typically, two blood (or urine) samples are collected: one just before administration of the dose, to determine the natural background levels, and the second sample after waiting a sufficient amount of time for penetration of the tracer within the compartment of interest. It is laborious and not very accurate, and is typically used only for reference with other measurement techniques.

There is therefore a need for a simple and highly accurate method and device for monitoring tissue hydration status that can be used in a broad range of field conditions.

SUMMARY OF THE INVENTION

Accordingly, it is an object of the present invention to overcome these and other drawbacks of the prior art by providing a novel method and device for monitoring tissue hydration and MWC by using a measurement of ultrasound velocity through tissue.

It is another object of the present invention to provide a lightweight, simple and convenient water content monitor device and method that can be used in the field and with battery-powered equipment.

It is a further object of the present invention to provide a temperature-compensated device and method for water content monitoring of tissue.

It is yet a further object of the present invention to provide a device and method for measuring the time-of-flight of the ultrasonic pulse transmitted through a selected tissue to assess its water content.

The present invention encompasses methods of detecting muscle hydration and water content with high accuracy, exploiting dependence of ultrasound propagation velocity on muscle molecular composition, affected dominantly by the content of water, which is the major molecular component of soft biological tissues.

The invention encompasses methods of detecting muscle hydration and water content by directly testing a selected muscle or group of muscles at a certain anatomical location. In a preferred embodiment, the device examines the soleus muscle (a large and accessible muscle in the human calf), where changes in water content can be easily detected.

The invention also encompasses a device for detecting muscle hydration and water content comprising a compact probe with miniature sensors, lightweight and elastic fixation elements on the extremity, portable electronic unit allowing monitoring of hydration status in field conditions without negatively affecting subject's performance.

Another specific embodiment provides for an additional procedure of measuring the temperature of tested muscle. A further specific embodiment provides for additional steps of measurement of ultrasound velocity at different sites of the body.

More specifically, the present invention encompasses methods of detecting muscle hydration and water content, comprising measurements of ultrasound velocity in the tested muscle using through-transmission method. The present invention also provides methods of detecting muscle hydration and water content comprising an additional step of analyzing the sequence of reflection of an ultrasound pulse from the boundaries between different tissues along the ultrasound propagation path. The present invention also encompasses methods of detecting muscle hydration and water content comprising additional procedure of evaluating separate contributions of muscle and other tissues along the ultrasonic path in the measured time-of-flight of the ultrasonic pulse.

BRIEF DESCRIPTION OF THE DRAWINGS

A more complete appreciation of the subject matter of the present invention and the various advantages thereof can be realized by reference to the following detailed description and drawings a brief description of which is followed.

DETAILED DESCRIPTION OF THE MOST PREFERRED EMBODIMENTS OF THE INVENTION

The MWC and dehydration assessment according to present invention is based on measurement of ultrasound velocity in tissue, which is defined by the molecular composition of tissue and to a good approximation, is a linear function of the water content. In several publications [Gorelov S E, Lyrchikov A G, Sarvazyan A P. *Ultrasound velocity in mammalian liver as a function of water content in tissue*. Acoustical Journal, 1981, 33, N. 2, 358–360; Sarvazyan A P, Lyrchikov A G, Gorelov S E. *Dependence of ultrasonic velocity in rabbit liver on water content and structure of the tissue*. Ultrasonics. 1987 July;25(4):244–247] incorporated herein by reference it was shown that the ultrasound velocity in soft biological tissues changes as a rate of about 3–4 m/s per 1% change of water content. It is also generally known that an easily achievable accuracy of general ultrasound velocity measurements is about 1 m/s. This suggests that a highly accurate detection of less than 1% of water content is possible by detecting a change in ultrasonic wave propagation.

Further physical foundation for this invention is given in the comprehensive review paper on mechanical and ultrasonic properties of soft tissues [Sarvazyan A. P. *Elastic properties of soft tissues*.—In: Handbook of Elastic Properties of Solids, Liquids and Gases, Volume III, Chapter 5, eds. Levy, Bass and Stern, Academic Press, 2001, 107–127.] It is shown that ultrasonic and mechanical parameters of soft tissues could be divided into two groups: one comprising parameters determined mainly by the molecular composition of tissues and the second comprising parameters that are more related to the features of higher structural levels. These two groups can be distinguished by comparing physical properties of intact tissue with those for homogenized tissue. Mechanical homogenization of tissue generally does not lead to substantial, immediate change in biochemical composition of tissue and has no significant effect on parameters determined by short-range inter- and intra-molecular interactions. For example, density and the bulk compression modulus K, which are mainly determined by the additive contributions of partial volumes of molecules composing the tissue, are not affected significantly by tissue disintegration. Transforming a tissue that has certain structure and rigidity into a structureless fluid obviously results in a dramatic change in the shear elasticity modulus G. At the same time, changes in the ultrasound velocity, which is a function of the density and bulk compression modulus K, after tissue homogenization is only about 1%. Hence, the ultrasound velocity is determined mainly by the molecular content of the tissue, and by short-range inter- and intra-molecular interactions. Consequently, from the point of view of ultrasound propagation parameters, soft tissues can be adequately modeled by a structureless fluid where only short-range inter-molecular interaction matters.

Molecular composition of tissues varies much less than their structure. Most soft tissues contain about 70–80% water. The remaining 20–30% of the tissue consists of major molecular components such as proteins and various organic and inorganic compounds of low molecular weight. These compounds are basically the same in different tissues and are often found in similar concentrations regardless of the tissue origin. In contrast, the range of variability of structural features among different tissues, such as geometrical parameters of cells and the degree of tissue mechanical heterogeneity and anisotropy are incomparably greater.

The ultrasound velocity (or the bulk elasticity modulus) is constant for most of the soft tissues within less than ±5%. Meanwhile, the structure-sensitive shear elasticity modulus for different soft tissues varies over four orders of magnitude and even within one tissue may change by hundreds of percent during such processes as an ordinary muscle contraction.

Figure 1:
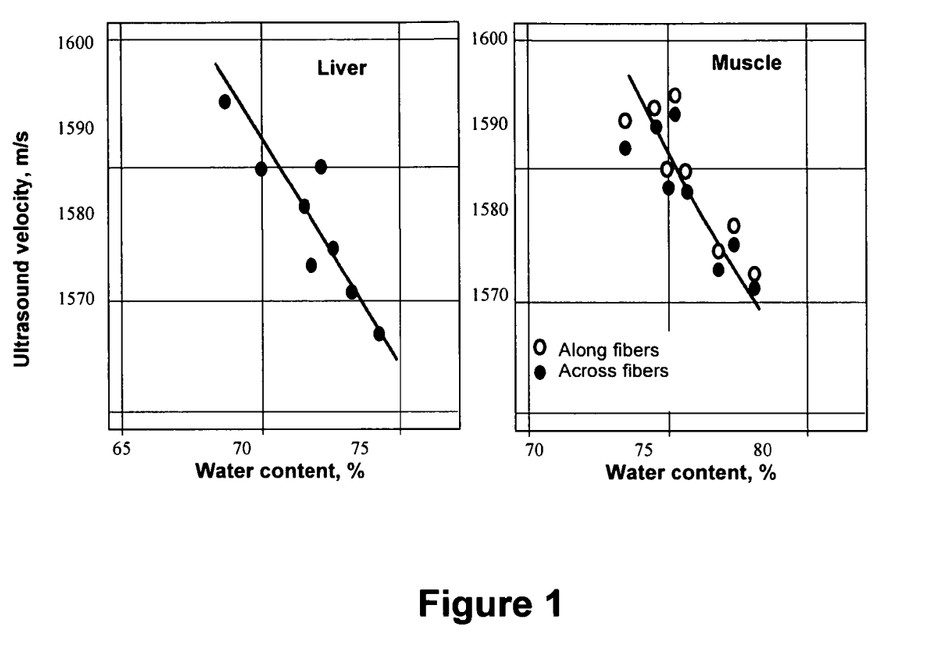
FIG. 1. Ultrasound velocity chart as a function of water content in animal liver and muscle.

Ultrasound propagation parameters were measured in a variety of biological tissues, particularly in samples from beef and pork undercuts, with respect to composition and structure. It was demonstrated that tissue biochemical (molecular) composition principally determines the velocity, while the structural and intracellular interactions are of less influence. If protein/fat ratio is a constant for the certain specimen, changes of the water content in intact or homogenized states is the main determinant of the velocity. FIG. 1 shows experimental results extracted from the publications [Gorelov S E, Lyrchikov A G, Sarvazyan A P. *Ultrasound velocity in mammalian liver as a function of water content in tissue*. Acoustical Journal, 1981, 33, N. 2, 358–360; Sarvazyan A P, Lyrchikov A G, Gorelov S E. *Dependence of ultrasonic velocity in rabbit liver on water content and structure of the tissue*. Ultrasonics. 1987 July;25(4): 244–247] for ex vivo animal tissues in intact condition at 25° C. The experimental data obtained on rabbit liver and beef skeletal muscle along and across fibers are given. The water content in the tissue samples was determined by dry to a constant mass at 110° C. with relative measurement accuracy of 0.5%. In liver tissue, the slope of the velocity graph versus the water content is about 3.5 m/s for 1% of water content. In muscle tissue, the water content varied in different samples from 73% to 78% and caused an averaged variation of the velocity of about 17 m/s, that is 3.4 m/s per 1% of MWC. These results form the basis for an approximate quantitative estimation that 1% change in MWC in human muscle at body temperature may cause a velocity shift of about 3 m/s (higher temperature leading to a lower slope of velocity vs. MWC). Such resolution can be easily achieved by the pulse time-of-flight technique on a base of about 10 cm.

Evaluation of ultrasound velocity in tissue requires parallel measurements of the acoustic path, l, and the ultrasonic pulse propagation time, t, the ratio of which, $c=l/t$, is the ultrasound velocity. As follows from experimental data illustrated in FIG. 1, the accuracy of the ultrasound velocity measurements necessary to detect a 1% change in MWC is about 3 m/s, that is, approximately 0.2% of the absolute value of c. To measure ultrasound velocity with this accuracy, a measurement is required of both l and t with an accuracy of about 0.1%. Taking into account that for a system shown in FIG. 1, $l\approx 10$ cm and $t\approx 700$ ns (for $c\approx 1,500$ m/s), the following requirements are calculated for the accuracy of measurements involved in the proposed method: 50–100 ns for measuring time-of-flight of the ultrasonic pulse, and 0.1 mm for the distance between transducers. Means for realizing these requirements are implemented in various embodiments of the invention described in more detail below.

Figure 2:
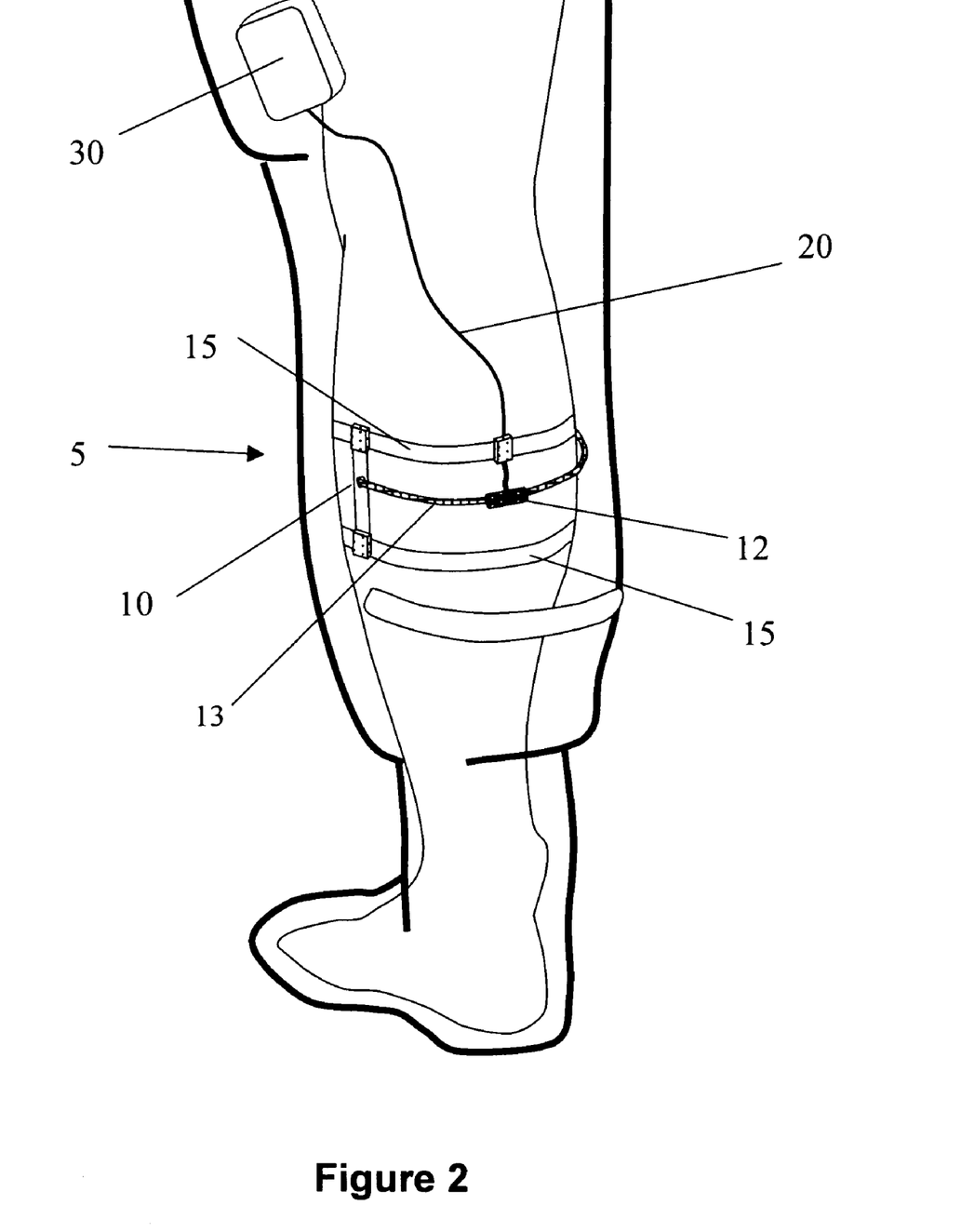
FIG. 2. MWC ultrasonic probe strapped to a human calf to assess water content in soleus muscle.
Figure 3:
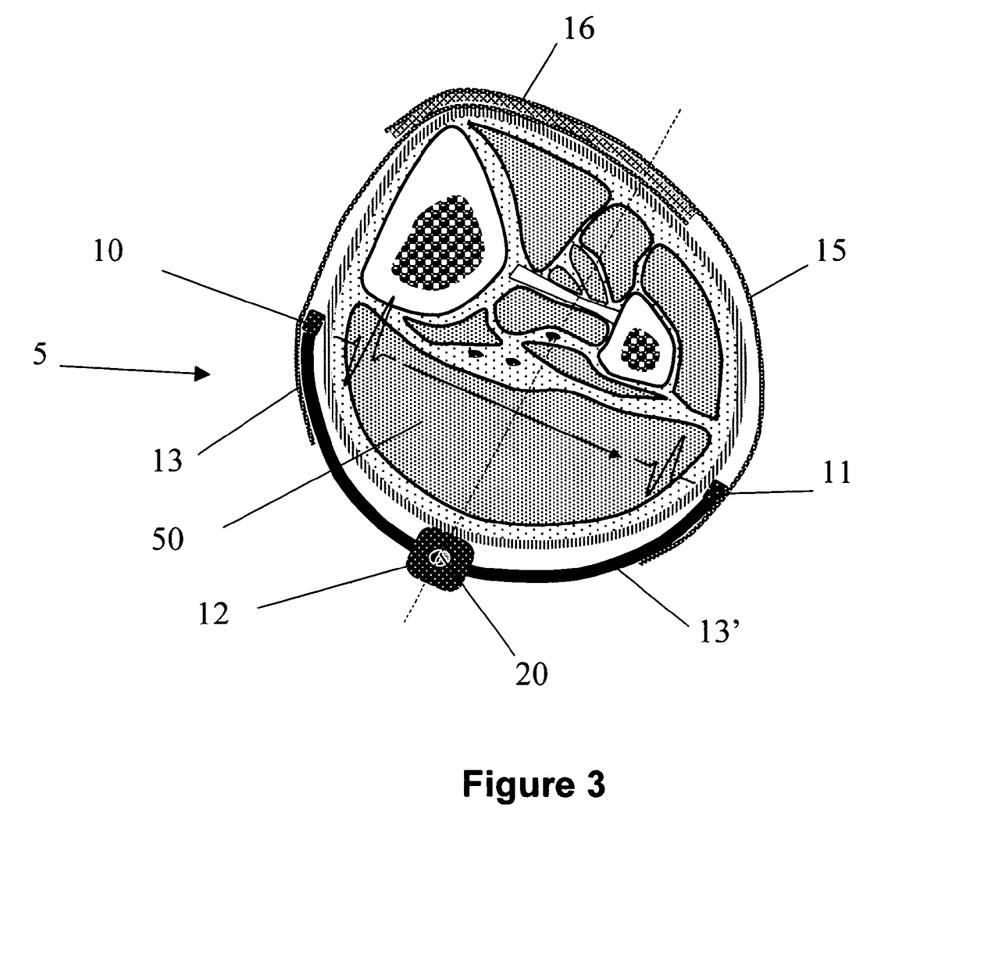
FIG. 3. Cross-sectional view of human calf with the strapped probe.

The general concept of the proposed MWC and dehydration monitor of the first embodiment of the invention is illustrated in FIGS. 2 and 3. They show an embodiment designed preferably for the use by soldiers during training or deployment. The probe is intended for application on a human calf and for examination of the soleus muscle therein. The positioning of probe and transducers in relation to anatomy of the cross-section is shown in FIG. 3.

The depicted MWC dehydration monitor is composed of a small lightweight probe 5 with miniature sensors 10 and 11 fixed on the soldier's calf by means of elastic straps 15. This load does not impede the soldier's work performance and can be placed on the body for all the time necessary for monitoring. The probe 5 is connected via cable 20 with a portable data acquisition and accumulation electronic unit 30 that is placed in a pocket or a special compartment in the soldier's uniform. The electronic unit 30 is battery-powered, has low power consumption, and could be connected to a common monitoring system via wire or wireless means.

This embodiment of the device can be used as a part of the wearable health-monitoring system. Such wearable devices are important for other potential users such as chronically ill patients, patients in the assisted-living and long-term care facilities.

Figure 4:
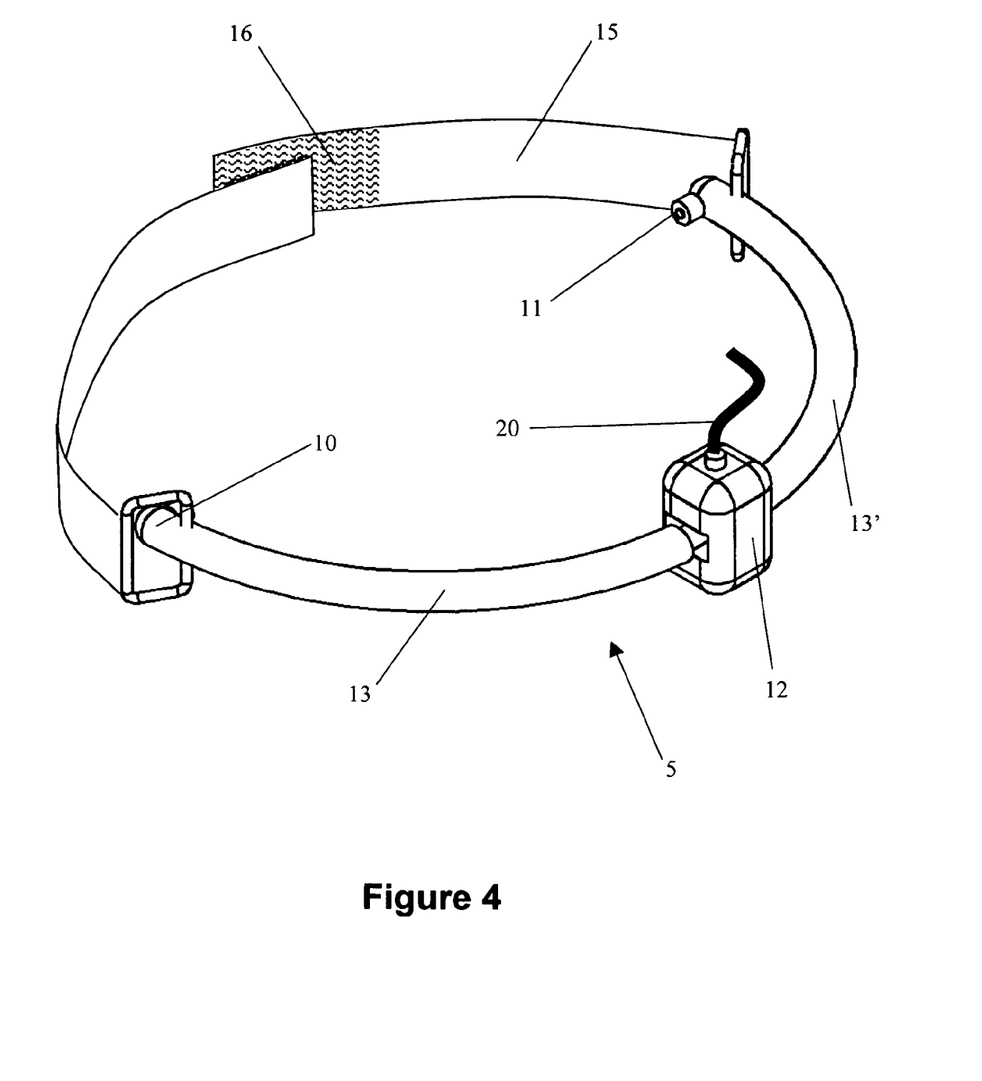
FIG. 4. Isometric view of a first embodiment of the MWC monitor probe.
Figure 5:
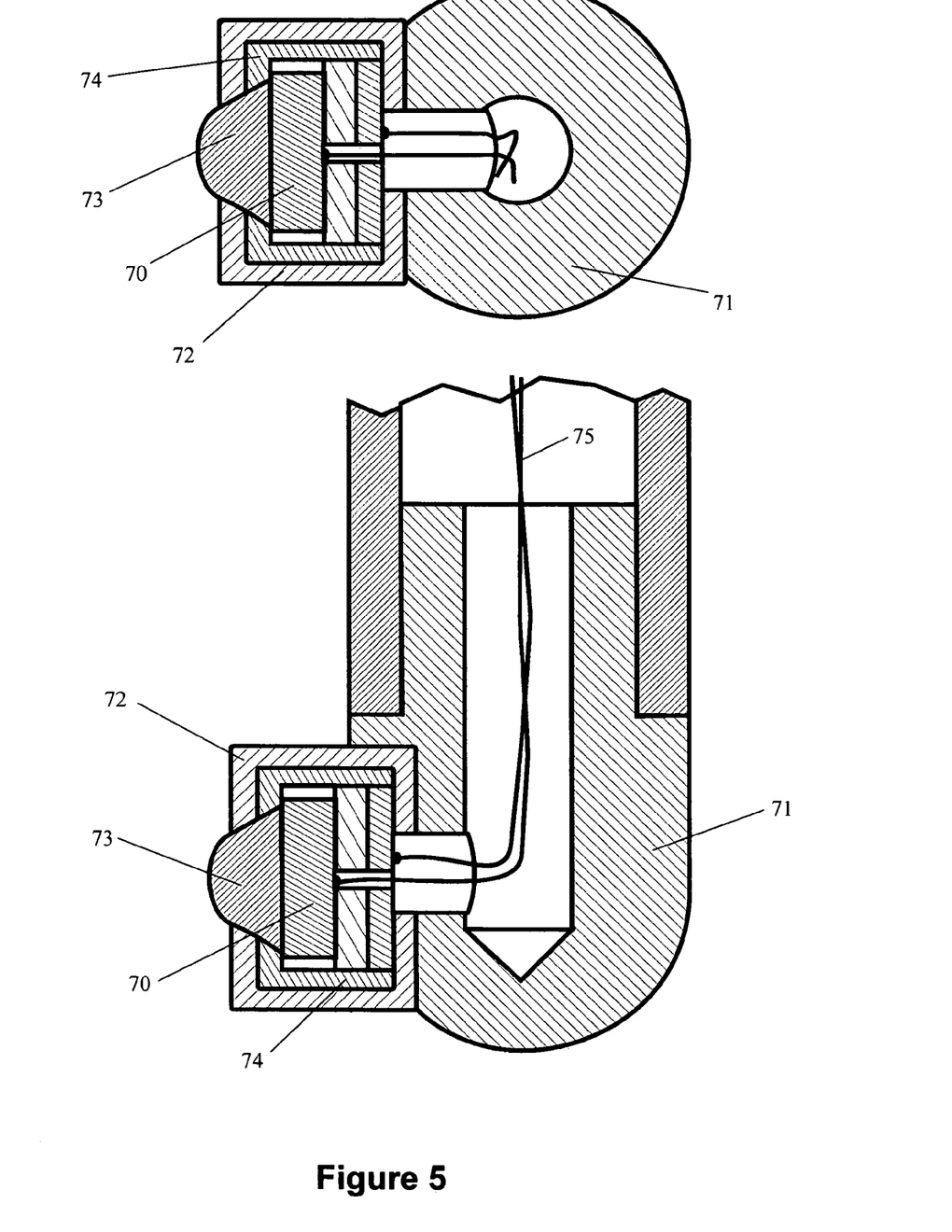
FIG. 5. Cross-sectional views of the ultrasonic transducer assembly of the first embodiment.
Figure 6:
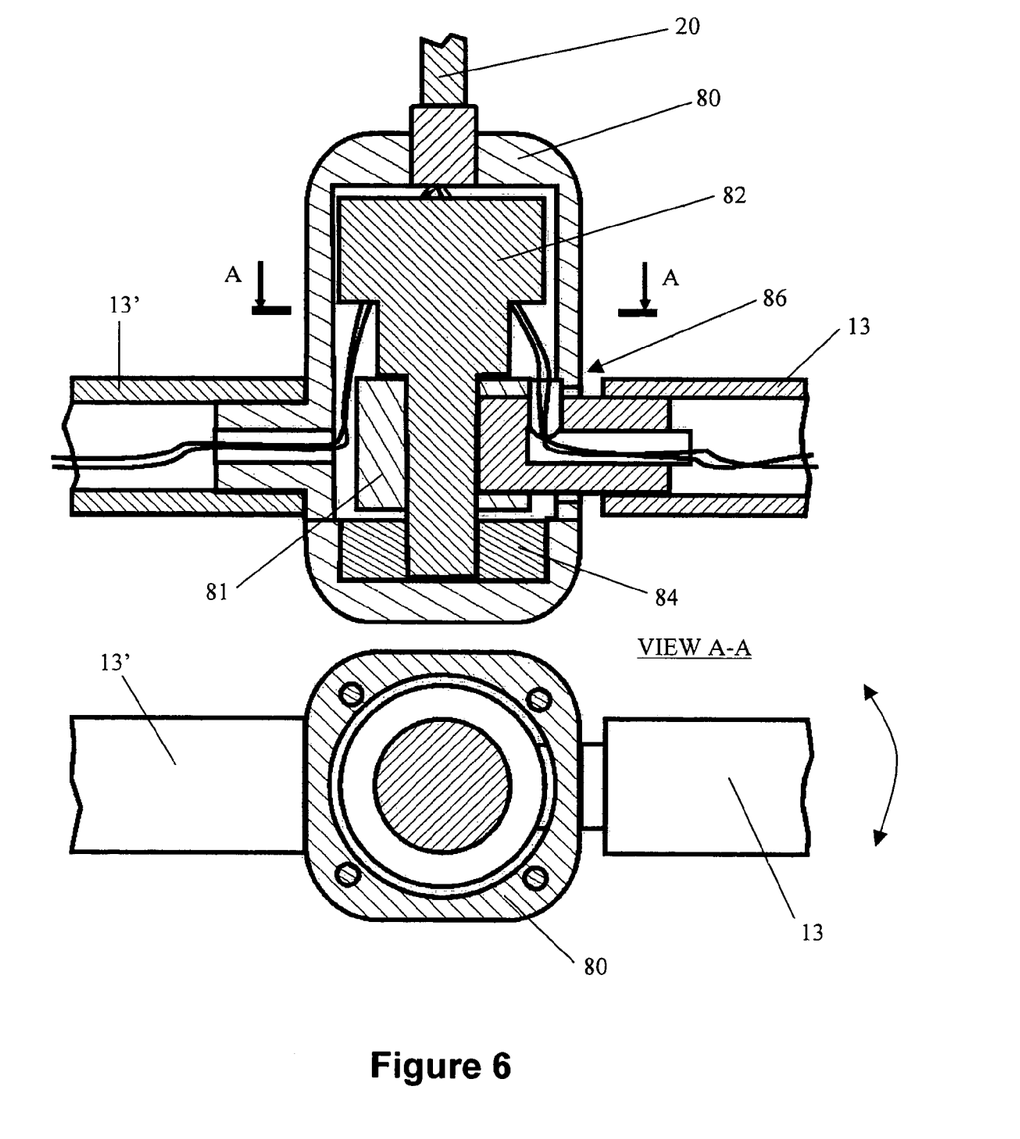
FIG. 6. Cross-sectional views of the angle sensor.
Figure 7:
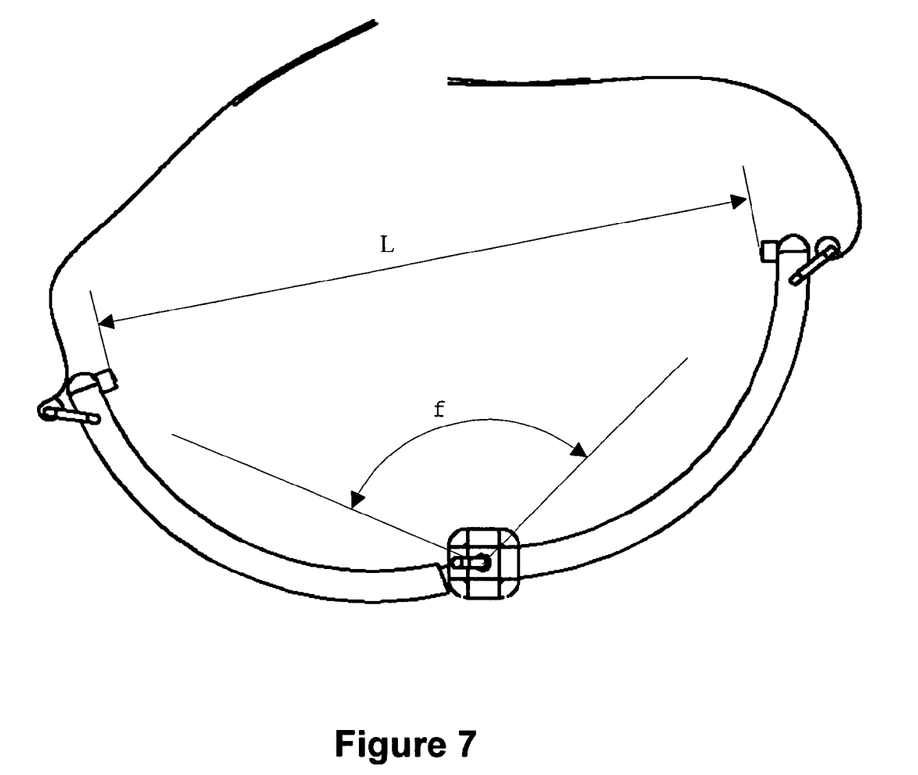
FIG. 7. Schematic diagram illustrating the calculation of the distance between the transducers.

General view of the water content monitor of the first embodiment of FIGS. 2 and 3 is presented in FIG. 4. The probe 5 includes:

Two miniature ultrasonic transducers: a transmitter 10 and a receiver 11, located coaxially to perform time-of-flight measurements of ultrasonic pulse propagation in a muscle. Cross-sectional view of the transducers is shown in FIG. 5, Two stiff but lightweight bearing tubes 13 and 13' to support the transducers 10 and 11 and to provide a geometrically definable acoustic base surrounding the human calf and placing the transducers 10 and 11 across the soleus muscle 50. A compromise between the tube's weight and necessary stiffness is important to provide both qualities—lightweight and absence of deformations capable of affecting distance readings, Angle sensor 12 for precise detection of variable angle between the tubes 13 and 13'. Cross-sectional view of the angle sensor 12 is shown in FIG. 6. The rotary hinge of the sensor allows probe adjustment to different subjects with varying width of extremity. Distance between transducers is calculated from the angle readings and the known exact distances between transducers' tips and the hinge center, as it is illustrated in FIG. 7. The angle sensor and the bearing tubes form an adjustable support system for the transducers 10 and 11, Elastic straps 15 with Velcro tape or a buckle 16 to fix the probe on the subject's extremity.

The ultrasonic transducers 10 and 11 are mounted at the ends of the bearing tubes 13 and 13' respectively, slightly standing out towards the surface of the patient's body to provide secure acoustical contact at a comfortable level of pressing. The transducers 10 and 11 can be preferably made of different types of piezoceramic such as PZT piezoceramic from Polytec PI, Inc., and Staveley Instruments, Inc. Connecting wires are placed inside the tubes 13 and 13'. The detailed design of the transducer is shown on FIG. 5. It includes a piezoelectric transducer element 70 contained in an insulator 74 and shield 72 such that the waveguide 73 is protruding therethrough for contacting the skin of the subject while still remaining in firm contact with the transducer 70. Transducer holder 71 is shaped to hold this subassembly in place while containing the electrical wires 75 designed to power up the transducer 70.

The range for the acoustic base, which may vary due to individual variations of the width of the calf cross-section in the medial-lateral direction is estimated at about 8–16 cm. To provide such distance changes, the angle between stiff bearing tubes 13 and 13' should vary within a certain range. Assuming necessary resolution of distance reading equal to 0.1 mm, the required resolution of angle measurements is about 0.1° Such resolution can be easily achieved with the use of resistive sensors based on the miniature precision potentiometers, such as for example 3310C-105-103 potentiometers of Bourns, Inc. (Riverside, Calif.) or more precise potentiometers from Nanotron, Inc. (Tempe, Ariz.).

Other available angle sensors can also be used in the embodiments of the present invention in place of the resistive sensors. Examples of appropriate angle transducers include fiber-optic sensors, capacitive sensors, piezoelectric sensors and strain gage based sensors.

The details of the angle sensor 12 are shown on FIG. 6. The sensor preferably consists of a housing 80 containing a precision potentiometer 82 firmly held with one of the bearing tubes, tube 13' in this case. The adjustable stem of the potentiometer is held in a bushing 81 firmly attached to the other bearing tube, tube 13 in this case. To complete the assembly, the stem is supported by a ball bearing 84. The housing 80 has an opening 86 wide enough to accommodate the range of motion of the bearing tube 13 as it swings from one extreme position to the other. Swinging of the bearing tube 13 changes the position of the potentiometer stem and therefore changes the resistance of the potentiometer, which can then be measured electrically and converted to the angle information signal.

Figure 8:
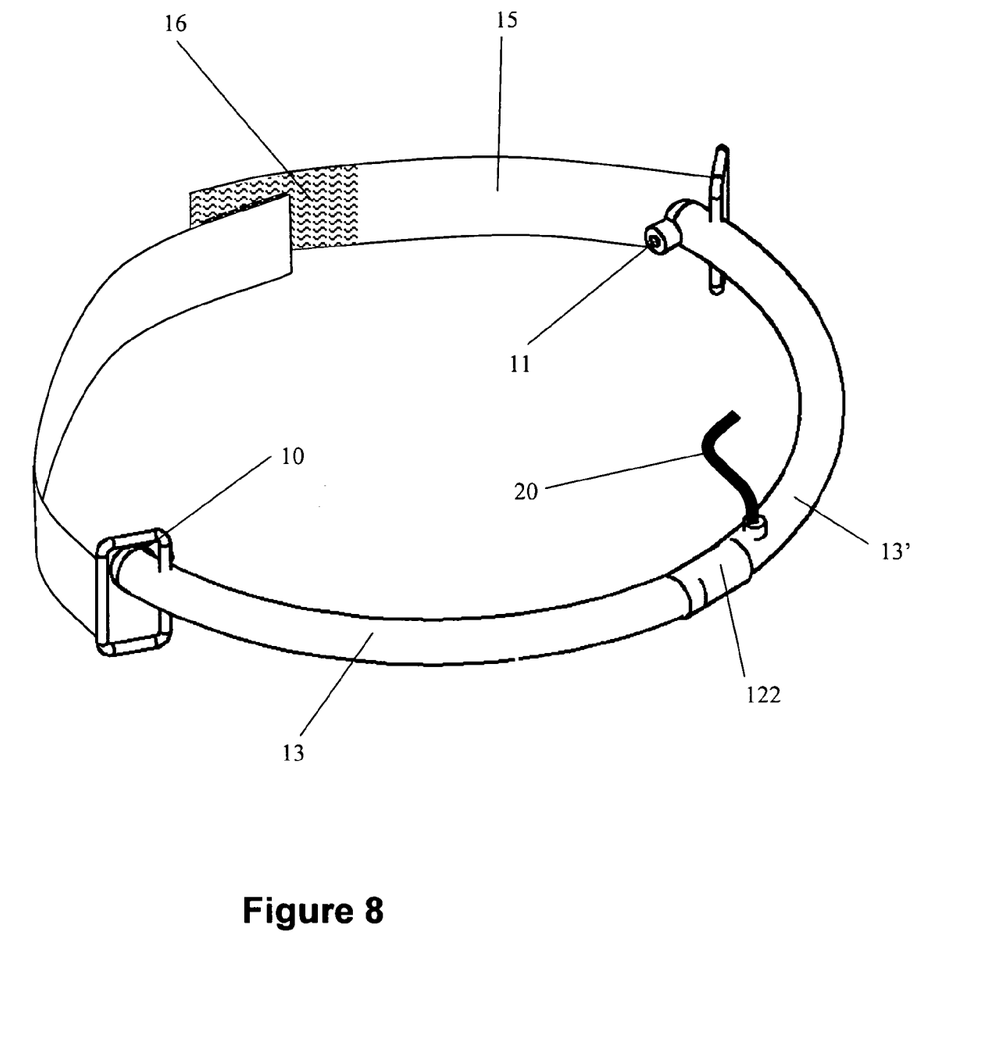
FIG. 8. Isometric view of a second embodiment of the MWC monitor probe.
Figure 9:
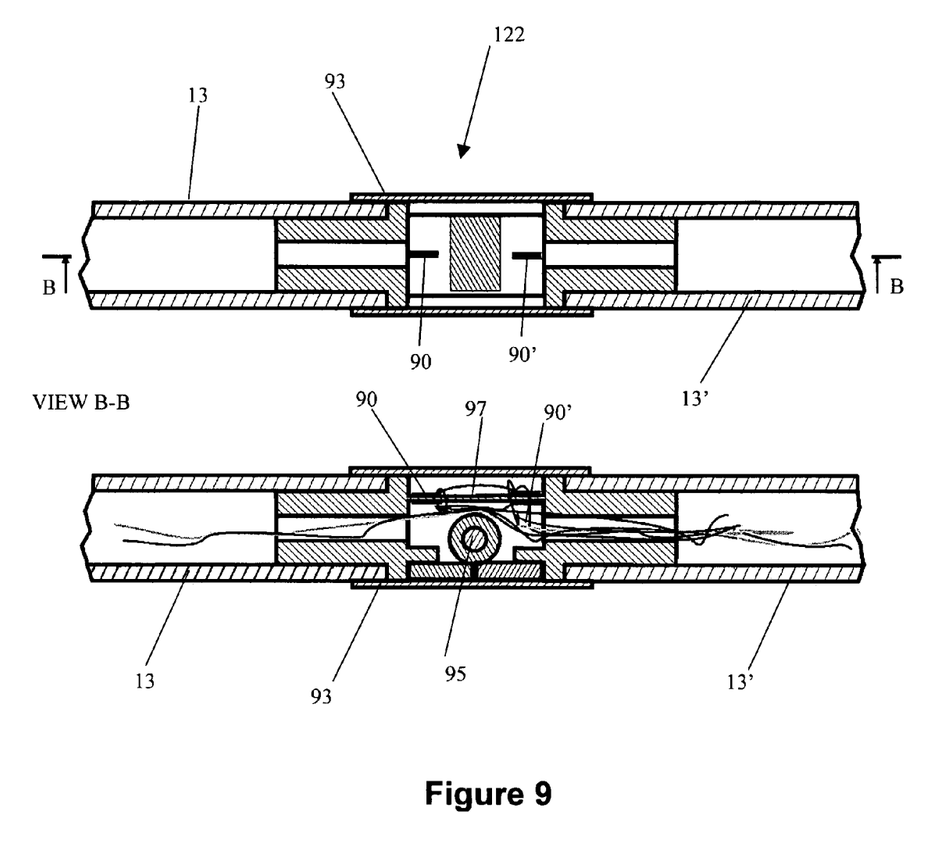
FIG. 9. Cross-sectional view of the angle sensor of the probe shown in FIG. 8.

A second embodiment of the MWC and dehydration monitor probe with a strain gage based angle sensor 122 is shown in FIG. 8. FIG. 9 shows a cross-sectional view of this angle sensor. The basic part of the sensor is a flat spring 97 with strain gages 90 and 90' glued on the surface of the spring 97. Various types of strain gages such as for example a semiconductor strain gage ESU-025-1000 (Entran, USA) can be used in this angle sensor. The housing of the angle sensor 122 is covered with an elastic cover 93. As one bearing tube 13 rotates about the other bearing tube 13' about the miniature hinge 95, the flat spring extends or contracts its length. That length extension is detected by the strain gages 90 and 90' and converted into the angle information since the geometry of the angle sensor 122 is known and fixed.

Figure 10:
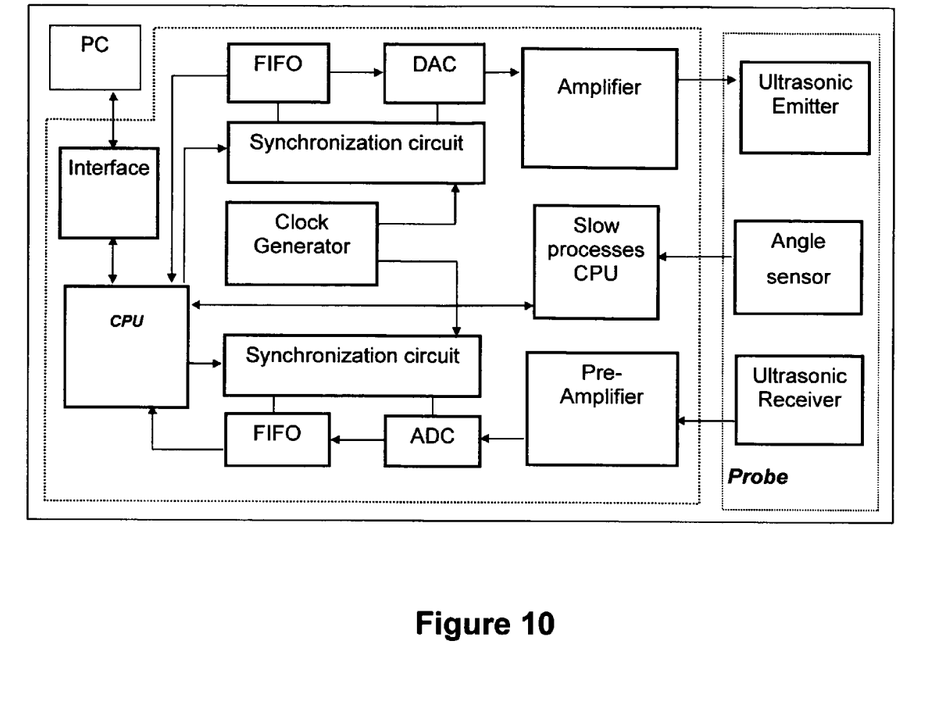
FIG. 10. Block-diagram of the water content monitor system of the first and second embodiments illustrated in FIGS. 2–9.

Embodiments of the water content monitor illustrated in FIGS. 2–9, can be operated with an electronic unit shown in FIG. 10. Block diagram of FIG. 10 shows one of possible embodiment of the MWC system capable of the angle sensor and ultrasonic data acquisition and analysis. Calculation of the ultrasound velocity and water content in tissue is performed by an external PC or by an internal microprocessor.

Various methods of ultrasonic pulse time-of-flight evaluation can be used. U.S. Pat. No. 6,468,215 issued to Sarvazyan et al. discloses some of the methods for evaluation of velocity of ultrasound pulse by the time-of-flight method. Wavelet analysis can be preferably employed for accurate evaluation of the pulse time-of-flight.

The method and device of MWC evaluation of this invention may be used for various anatomical sites of the body. At some measurement sites, where the ultrasonic pulse crosses not only muscles but also layers of other tissue such as fat and connective tissue, a different embodiment of the device can be used. In that embodiment, information on the time-of-flight is evaluated separately in every layer and respective corrections for the MWC assessment are made. This is achieved with the use of conventional A-mode pulse-echo ultrasonic measurement method.

A variation of the water content monitor of the invention designed for this measurement would include an arrangement similar to that shown in FIG. 4 or 8, but with only one ultrasound transducer used. Instead of the second transducer, a simple ultrasound reflecting plate is mounted on the opposite arm of the probe. Ultrasound transducer, after emitting a short pulse, is switched to a receiving mode. Reflections from all tissue boundaries along the ultrasonic pulse are therefore detected. This allows obtaining the time-of-flight in each tissue layer separately, including solely through the muscle.

An optional temperature probe addition to the water content monitor of the invention is described below in more detail. One of the factors that can influence the measurement accuracy is temperature dependence of ultrasound velocity in soft tissues. The temperature dependencies of bulk elasticity modulus and ultrasound velocity in tissues are closely related to that of water with anomalous positive temperature slope at room or body temperatures. The temperature slope of ultrasound velocity in soft tissues at body temperature is less than 2 m/s per 1° C., which corresponds to a change of ultrasound velocity in tissue caused by about 0.7% of MWC. For higher accuracy of measurement of MWC, the temperature dependence of ultrasound velocity needs to be taken into account in the ultrasonic MWC monitor. In any of the embodiments discussed herein, a miniature optional temperature sensor attached to the measuring site of the muscle can be used. The sensor capable of measuring local temperature with an accuracy of a few tenths of 1° C. enables to fully account for the temperature changes in the tested muscle.

Figure 11:
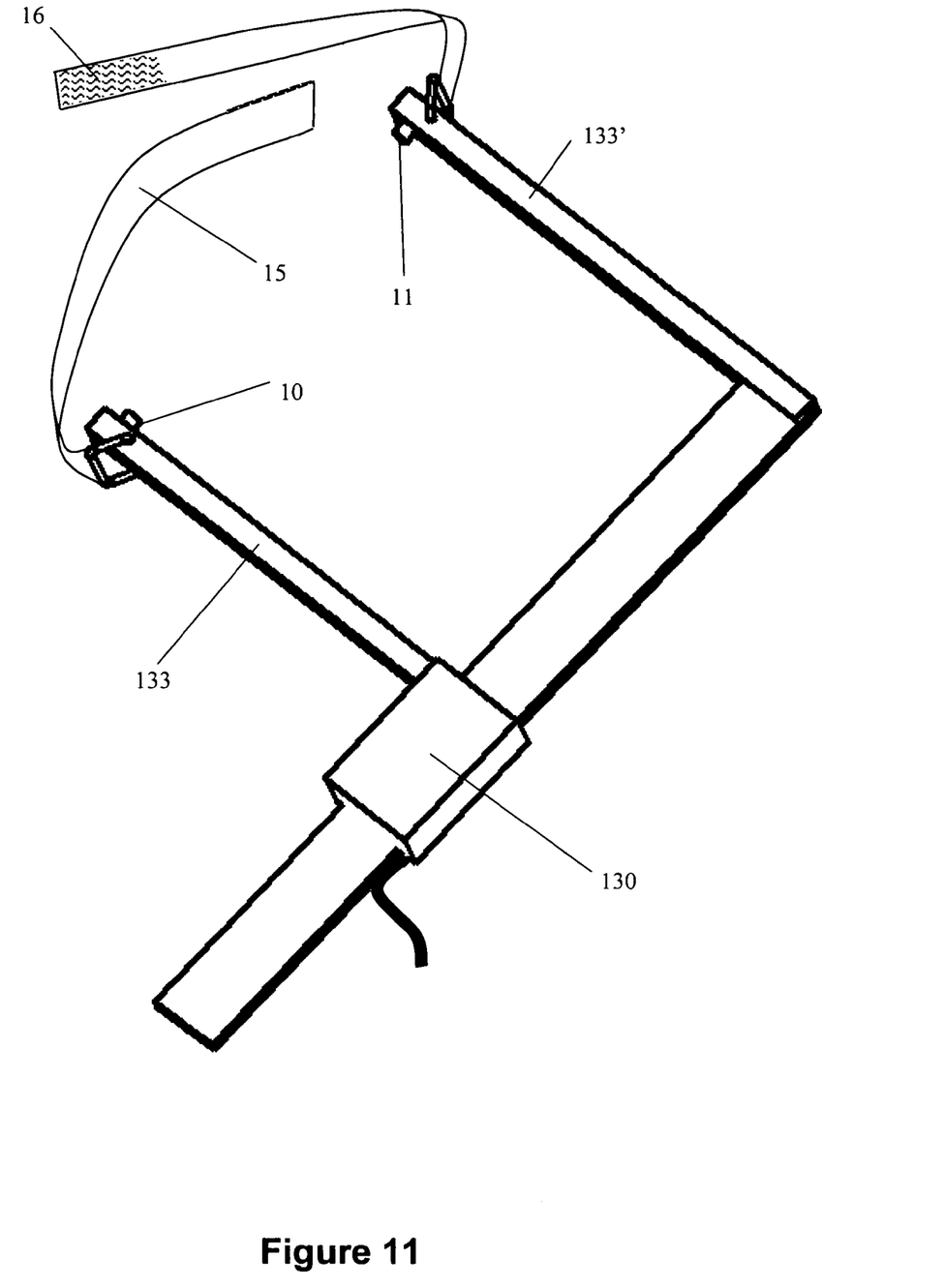
FIG. 11. Isometric view of a third embodiment of the water content monitor probe.

Other types of the acoustic path meters can be employed in any of the embodiments discussed herein. FIG. 11 shows an example of the MWC probe where the acoustic path is measured using a slide gage similar to that used in digital calipers. Distance measuring unit 130 continuously detects the distance between the transducers 10 and 11 supported by caliper jaws 133 and 133'.

The ultrasonic water content monitor of the present invention advantageously differs from the existing bioelectrical impedance and conductance methods by:

Higher sensitivity and accuracy;
Independence of testing results on the electrolyte balance;
Independence of results on size of extremity and other anthropometrical parameters;
Possibility to assess changes of water content in muscle at a certain anatomical location.

The device of the present invention could be advantageously used to monitor patients with a wide variety of conditions resulting in changes in individual's water content level including significant physical changes in body fluids retention pre- and post-surgery, digestion problems, high blood pressure, muscle cramps, obesity, etc. It may also provide a convenient, lightweight system for use in sports medicine, health and exercise clubs for monitoring total body hydration during long-term endurance exercise or performance in hot conditions.

One of important additional uses of the device of the invention is to assess development of edema. Edema is a major symptom for many common diseases. It is a swelling caused by the accumulation of fluid in intracellular spaces of the body. While dehydration decreases cognitive and physical work capabilities, excessive hydration resulting in edema is a common symptom of cardiac, hepatic or renal pathology, malnutrition and many other pathologies and diseases. Edema causes muscle aches and pains and may affect the brain, causing headaches and irritability. Edema is a major symptom for deep venous thrombosis, it may be caused by allergies or more serious disorders of the kidney, bladder, heart, or liver, food intolerance, poor diet (high sugar & salt intake), pregnancy, abuse of laxatives, diuretics, drugs, by contraceptive pills, hormone replacement therapy, phlebitis, etc.

Changes in muscle water content are correlated with multiple disorders, particularly in aging population that is frequently confined to their homes. The technology of the present invention may find an ample additional use as at home-monitoring and telemedicine device for the remote assessment of patients.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An ultrasonic tissue water content monitor comprising:
   a first ultrasonic means,
   a second ultrasonic means, and
   an adjustable support system to hold said first ultrasonic means and said second ultrasonic means against said tissue at a known distance therebetween, said adjustable support system including:
      a first bearing tube having a first end and a second end and defining a first distance therebetween, said first end supporting said first ultrasonic means,
      a second bearing tube having a first end and a second end and defining a second distance therebetween, said first end supporting said second ultrasonic means, and
      a rotary hinge with an angle sensor, said hinge attached to said second end of said first bearing tube and said second end of said second bearing tube to hingedly connect said both bearing tubes, said angle sensor providing angle information of said first bearing tube relative to said second bearing tube,
   whereby the distance between said first and second ultrasonic means can be calculated from said known first distance, said second distance and said angle information.

2. The monitor as in claim 1 further equipped with an elastic strap to hold said adjustable support system and said first and second ultrasonic means about said tissue.

3. The monitor as in claim 1, wherein said first ultrasonic means is an ultrasonic transmitter and said second ultrasonic means is an ultrasonic receiver.

4. The monitor as in claim 1, wherein said first ultrasonic means is an ultrasonic transducer and said second ultrasonic means is an ultrasonic reflecting plate.

5. The monitor as in claim 1, wherein said adjustable support system further equipped with an adjustable strap means to complete the loop about said tissue for attaching said monitor thereto.

6. The monitor as in claim 1, wherein said rotary hinge equipped with a flat sprig and said angle sensor comprising a strain gage attached to said flat spring.

7. The monitor as in claim 1 further equipped with a tissue temperature sensor.

8. A method of evaluating water content in tissue comprising the steps of:
   (a) providing a first ultrasonic means held against said tissue on one side of a predetermined measurement pathway, and a second ultrasonic means held against said tissue on the other side of said predetermined measurement pathway, said second ultrasonic means located at a known distance from said first ultrasonic means, said predetermined measurement pathway selected to traverse only a portion of said tissue in which velocity of ultrasound wave pulse propagation is substantially uniform therethrough.
   (b) transmitting an ultrasound wave pulse across said tissue from said first ultrasonic means to said second ultrasonic means,
   (c) detecting time-of-flight of said wave pulse between said first and said second ultrasonic means;
   (d) calculating ultrasonic velocity of said wave pulse through said tissue from said time-of-flight and said distance between said first and said second ultrasonic means; and
   (e) calculating water content of said tissue from said calculated ultrasonic velocity.

9. The method as in claim 8 further comprising the steps of:
   (f) measuring tissue temperate, and
   (g) correcting the water content value from step (e) by a factor defined by said tissue temperature.

10. The method as in claim 8, wherein step (a) further including providing an adjustable support system to hold said first ultrasonic means and said second ultrasonic means against said tissue at said known distance therebetween.

11. The method as in claim 8, wherein said tissue is soleus muscle.

12. The method as in claim 8, further including a step of transmitting said calculated water content to a remote location.

13. The method as in claim 12, wherein said transmitting step including a wireless transmission.

14. A method of evaluating water content in tissue comprising the steps of:
   (a) providing a first ultrasonic means held against said tissue on one side of a predetermined measurement pathway, and a second ultrasonic means held against said tissue on the other side of said predetermined measurement pathway, said second ultrasonic means located at a known distance from said first ultrasonic means, said predetermined measurement pathway selected to traverse at least two layers of said tissue, each layer characterized by velocity of ultrasound wave pulse propagation being substantially uniform therethrough;
   (b) transmitting an ultrasound wave pulse across said tissue from said first ultrasonic means to said second ultrasonic means;
   (c) detecting a plurality of time-of-flight measurements of said wave pulse within each layer of said tissue;
   (d) calculating a plurality of ultrasonic velocity measurements of said wave pulse through each layer of said tissue from said time-of-flight measurements and said distance between said first and said second ultrasonic means; and
   (e) calculating water content of said tissue from said calculated ultrasonic velocity.

15. The method as in claim 14, wherein said steps (c) through (e) are done using an A-mode pulse-echo ultrasonic measurement method.

* * * * *

UNITED STATES PATENT AND TRADEMARK OFFICE
CERTIFICATE OF CORRECTION

| | | |
|---|---|---|
| PATENT NO. | : 7,033,321 B1 | Page 1 of 1 |
| APPLICATION NO. | : 10/979940 | |
| DATED | : April 25, 2006 | |
| INVENTOR(S) | : A. P. Sarvazyan | |

It is certified that error appears in the above-identified patent and that said Letters Patent is hereby corrected as shown below:

In the specification: insert before the words "BACKGROUND OF THE INVENTION" the following text:

--STATEMENT REGARDING FEDERALLY SPONSORED RESEARCH OR DEVELOPMENT

This invention was made with government support under contract W81XWH-04-C-0036 awarded by Army/MRMC. The government has certain rights in the invention.--

Signed and Sealed this

Second Day of December, 2008

JON W. DUDAS
*Director of the United States Patent and Trademark Office*